United States Patent [19]

Bermant

[11] 4,165,747
[45] Aug. 28, 1979

[54] MICROVASCULAR CLAMPS WITH SUTURE RETAINING MEANS

[75] Inventor: Michael A. Bermant, Chicago, Ill.

[73] Assignee: Division of Plastic Surgery of the Medical School of Northwestern University, Chicago, Ill.; a part interest

[21] Appl. No.: 763,575

[22] Filed: Jan. 28, 1977

[51] Int. Cl.² .................................................. A61B 17/11
[52] U.S. Cl. .................................. 128/334 C; 128/346
[58] Field of Search .................... 128/325, 326, 334 R, 128/334 C, 335, 340, 346, 321, 322; 24/263 SB

[56] References Cited

U.S. PATENT DOCUMENTS

| | | | |
|---|---|---|---|
| 1,664,112 | 3/1928 | Junemann | 128/325 |
| 2,108,325 | 2/1938 | Ziegler | 128/346 |
| 3,446,212 | 5/1969 | LeRoy | 128/346 X |
| 3,868,957 | 3/1975 | Doddington | 128/346 |
| 3,911,926 | 10/1975 | Peters | 128/325 |

FOREIGN PATENT DOCUMENTS 618821  4/1961  Canada ................................... 128/346
395074  1/1974  U.S.S.R. ............................... 128/334 C

OTHER PUBLICATIONS

Acland, Surgery vol. 75, No. 2, pp. 185–187.

Primary Examiner—Dalton L. Truluck
Attorney, Agent, or Firm—Hill, Van Santen, Steadman, Chiara & Simpson

[57] ABSTRACT

Apparatus having parallel-closing jaws for clamping and immobilizing ends of blood vessels to be joined together by suturing without damaging the vessel walls. A spring biasing the jaws together is adjustable to exert no more than 30 gm/cm² in squeezing force to vessel walls in each clamp. A stay suture retainer affixed to one or more of the jaws of the apparatus receives ends of two stay sutures passed through the ends of the blood vessels to draw them together, to immobilize the vessel ends with respect to the apparatus during close, finish suturing thereof. Mayfield-type and threaded-shaft clamp pairs are disclosed, each connected to and selectively slidable along a rigid bar for adjustable spacing upon the ends of the vessels to be joined. The clamps are durable and comprise a single piece to facilitate use.

20 Claims, 8 Drawing Figures

U.S. Patent   Aug. 28, 1979   Sheet 1 of 2   4,165,747
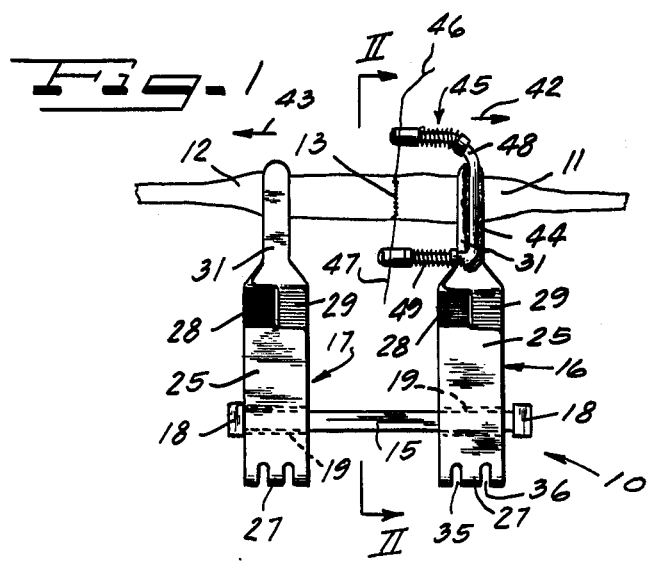
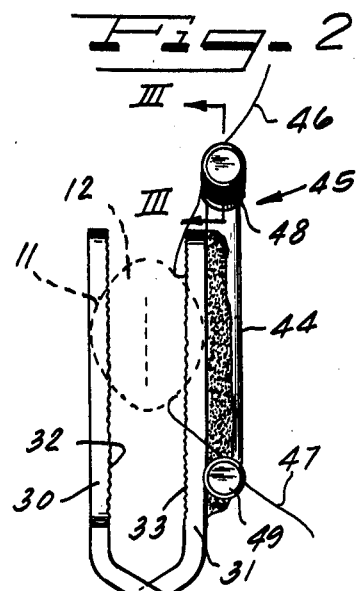
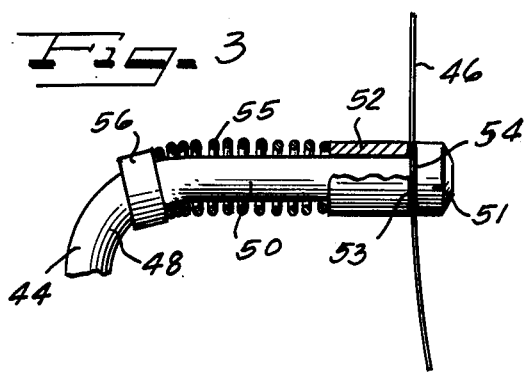
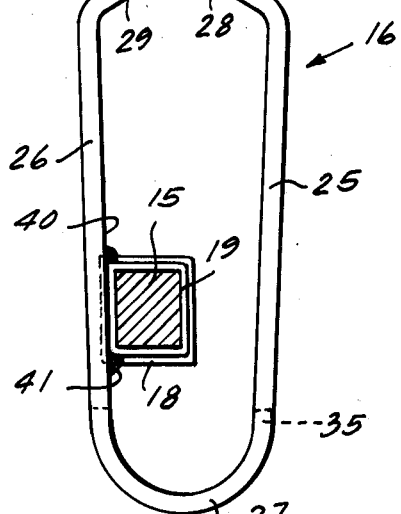
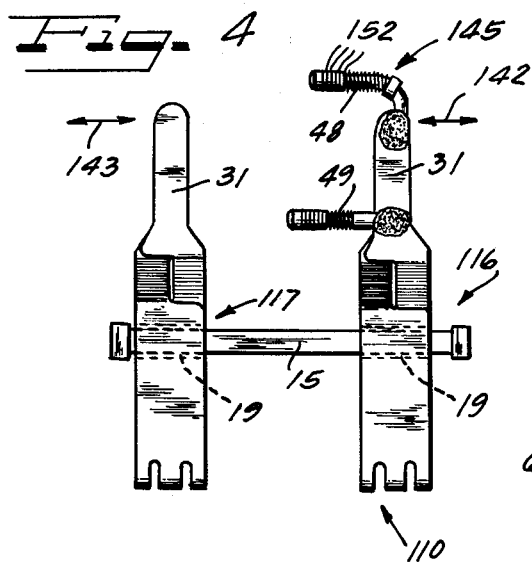
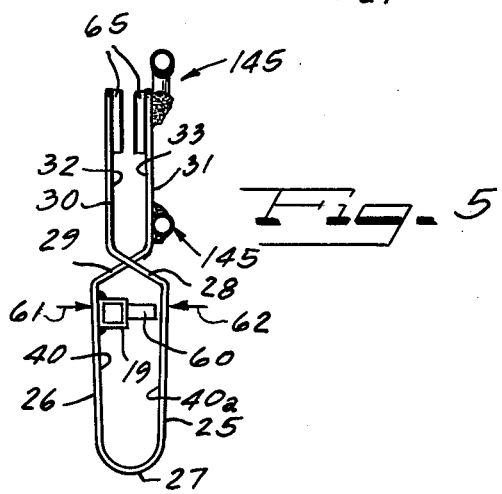

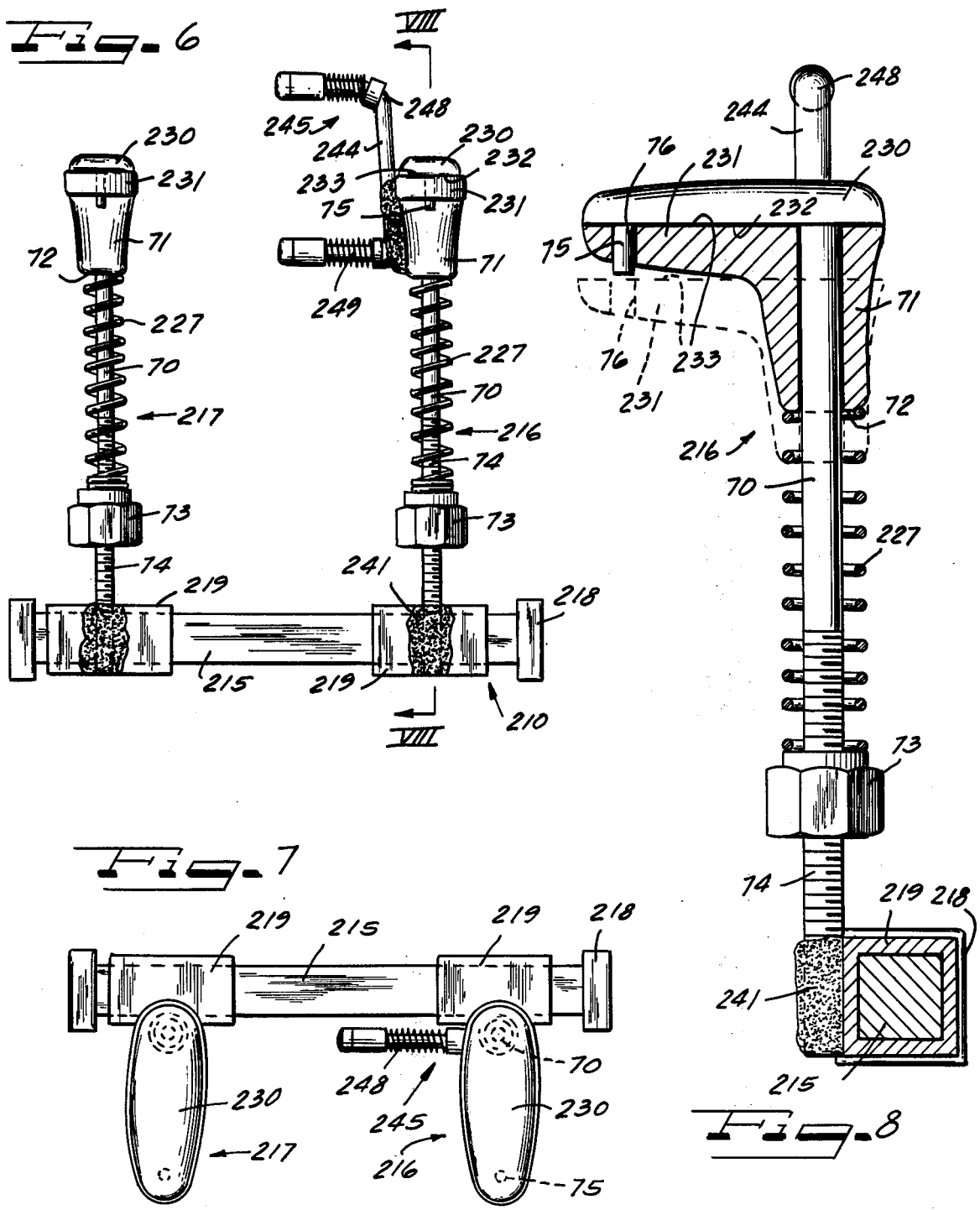

MICROVASCULAR CLAMPS WITH SUTURE RETAINING MEANS

BACKGROUND OF THE INVENTION

1. Field of the Invention

The present invention relates to microsurgical clamps for surgical attachment of blood vessel ends by suturing thereof.

2. The Prior Art

Microvascular surgical clamps for use in microscopic anastomosis of severed ends of blood vessels are well known in the art especially from the medical literature. As described in Ostrup, et al, 10 Plastic and Reconstructive Surgery 18-28, "Microvascular Surgery" (1976), joining of severed veins or artery ends by sutures is well established. Any of a number of double microvascular clamps described in the literature may be employed, including those of Acland, 75 Surgery 185, "Microvascular Anastomosis: a device for holding stay sutures and a new vascular clamp"; Henderson et al., Medical Journal of Australia (Apr. 4, 1970, pages 715-16), "An Adjustable Double Microvascular Clamp"; Zirkle, et al., 51 Plastic and Reconstructive Surgery 340-41, "An Adjustable Double Clamp for use in Microvascular Surgery", to clamp two blood vessel ends and to hold them in a desired relationship. Two stay sutures are placed through the front walls, 120° apart, to join the vessel ends. Close sutures placed between the two stay sutures join the wall ends between the stay sutures. The double clamps are then rotated through 180°, with one stay suture passed over and one under the blood vessel. Then the other 240° of the vessel wall is repaired with further sutures.

Of the clamps described in the Ostrup and other literature, only the Acland clamp shown in the 1974 Surgery article has a stay suture retention device. The Acland device has a pair of center-pivot type clamps held in spaced relation by crossed wires forming a nautical-type cleat about which the stay sutures are wrapped and jammed for retention. The Henderson clip has laterally separable clamps of a rear pivot type which are closed by screwing a threaded nut at the base of the jaws. A clamp by Buncke has angled clamps engaging a square shaft at an angle, but having substantially parallel jaws. Neither the Henderson nor the Buncke devices have stay suture retainers thereon. Surgeons employing such clamps must employ any of several methods for immobilizing the stay sutures with respect to the blood vessel during close suturing thereof, as described in the Ostrup article.

Of the prior patented art, U.S. Pat. No. 3,911,926 discloses an adjustable microvascular U-shaped clamp wherein a pair of Mayfield-type clamps are received about a bar having capped ends, the clamps being maintained in position by a covering thereover and a clamp opener engaged therewith. U.S. Pat. No. 3,509,882 shows a comparatively large, parallel-jaw spring clip, wherein a spring within a tubular body transverse to fixed amd movable jaws acts to close a vessel placed therebetween.

None of the prior patented or published art shows a microvascular surgical clamp having eight ideal features as identified in an article by Thurston, et al., Plastic and Reconstructive Surgery (February, 1976), at 202. Such features include small size, light weight, mechanical simplicity, flat jaws coated with a non-slip surface, maximum pressure of 30 grams per square centimeter together with an ability to be calibrated for lesser pressures, and durability for repeated use.

SUMMARY OF THE INVENTION

A microvascular surgical clamp apparatus comprises an elongate rigid bar with a pair of clamps spaced apart along the bar, each carrying a pair of substantially parallel-closing, relatively-movable jaws. Guide brackets on each of the clamps retain the clamps on the bar in transverse relation thereto and in a substantially coplanar relationship to one another. One or both of the guide brackets may be slidable upon the bar so that the spacing of the clamps may be adjusted. A spring on each clamp biases at least one of the relatively movable jaws of each pair into contact with the other.

Further in accordance with the invention, a stay suture retainer is affixed to the pair of clamps to extend substantially in the plane of the clamps and the bar. The retainer comprises first and second arms each affixed one of the jaws and spaced adjacent but on opposite sides of a line extending between the contact surfaces of the jaws of the clamps. Each of the first and second arms carries an attachment device thereon for removably engaging a stay suture joining the blood vessel ends.

In a first embodiment, a pair of pressure-openable, Mayfield-type clamps are provided, each having a pair of elongate graspable portions joined together at rearward ends thereof by a rounded, slotted spring, and joined to opposing jaws by a pair of crossed connecting portions. A force applied to the graspable portions against the bias of the spring will move the portions together and open the jaws. Positioning of a slidable guide bracket within the clamp along the graspable portion thereof toward the spring will permit the jaws to resist sideward forces, as is necessary when blood vessel ends are to be joined under tension; placing the guide bracket adjacent the crossed connecting portions will not develop a sufficient torque on the guide bracket from the jaws to cock the bracket on the bar, to allow the clamp to slide in response to a lateral force on the jaw end. This latter arrangement is preferred where the surgeon wishes to adjust clamp spacing during an operating procedure.

In a second embodiment of the apparatus, very small clamps are provided, each having a threaded shaft carrying on one end thereof a fixed jaw. A second jaw with a collar for movement along the shaft is biased against the first jaw by a coil spring. The spring is bottomed against an axially-movable nut threaded onto the shaft. A stay suture retainer in U-form may be attached to the collar portion of the second jaw for use as in the first embodiment.

THE DRAWINGS

FIG. 1 is a plan view of a first embodiment of the invention in use with ends of a blood vessel.

FIG. 2 is a sectional view through the clamp apparatus of FIG. 1 on line II—II.

FIG. 3 is a sectional view through a first arm of the stay suture retainer of FIG. 2, on line III—III.

FIG. 4 is a top plan view of a second embodiment of the invention, similar to FIG. 1.

FIG. 5 is a side elevational view of an individual clamp from FIG. 4.

FIG. 6 is a top plan view of a third embodiment of the present invention.

FIG. 7 is an end elevational view on line VII—VII of FIG. 6.

FIG. 8 is a longitudinal sectional view on line VIII—VIII of FIG. 6.

THE PREFERRED EMBODIMENTS

A microvascular surgical clamp apparatus is shown in a first embodiment at 10 in FIG. 1, with ends 11 and 12 of a blood vessel which are being connected together by a circumferential line of sutures 13. The clamp apparatus 10 comprises an elongated rigid bar 15 which joins together a first clamp 16 and a second clamp 17 in a U-shape or form. The rigid bar 15 is preferably a noncylindrical form such as a square as shown in FIG. 2 in order that the clamps 16, 17 will be maintained in a coplanar relationship with one another without swiveling about the bar 15. The bar 15 further is of a uniform cross section, except for end caps 18, 18 of increased size on either end thereof, in order that the clamps 16, 17 may be selectively spaced individually therealong by means of guide means such as guide brackets 19 affixed to each clamp 16, 17 and having a close sliding engagement with the bar 15.

Each of the clamps 16 is in the form of a modified Mayfield clamp, comprising a pair of graspable portions 25, 26 joined together at a rearward end by a round, slotted spring 27. First and second crossed connecting portions 28, 29 on respective forward ends of the graspable portions 25, 26 connect substantially parallel-closing, relatively movable first and second jaws 30, 31. Interior surfaces 32 and 33 of the jaws 30, 31, respectively, are treated with a non-slip surface as by a grooving or sandblasting process.

In accordance with the principles of the invention, the round, slotted spring means 27 on the rearward end of the clamp 16 or 17 is longitudinally slotted to remove material as at 35, 36 in FIG. 1, to reduce the maximum possible biasing force exerted by the spring 27 to close the inner contact surfaces 32, 33 of the jaws 30, 31 together. As demonstrated in the Thurston article, supra, a squeezing force in excess of 30 grams per square centimeter will permanently damage a blood vessel wall and must be avoided. In a Mayfield clamp having a width of 3.3 mm removal of two slots of about 0.6 mm width each has been found effective to so control the maximum spring bias. Manipulation of the spring 27 can further reduce the maximum force exerted, as where only very thin blood vessels are to be worked with. Since the jaws 30, 31 close substantially parallel to one another, also in accordance with the principles of the invention, for any given vessel size the maximum pressure thereon exerted by the spring 27 can be readily determined by a simple force measurement at the tips of the jaws 30, 31.

As further shown in FIG. 2, the guide bracket 19 is affixed to an inner surface portion 40 of one of the graspable portions 25, 26, as by brazing or soldering at 41. The guide bracket 19 is in the form of a circumferentially-closed sleeve, to insure a close but slidable fit about the bar 15 without maintenance of specific tolerances between the bracket 19 and the surface 40 of the clamp 16. Further, in this first embodiment, as shown in FIG. 2, the guide bracket 19 is fixed to the graspable portion 26 closely adjacent the spring 27 and spaced well apart from the tips of the jaws 30, 31. Such spacing from the jaws 30, 31 assures that friction between the bracket 19 and bar 15, especially from the cocking of same, will be sufficient to oppose a separating force 37 or 38 imposed on the jaws of the clamps by any necessary elongation or stretching of the blood vessel ends 11, 12 for connection at the line 13.

Also in accordance with the principles of the present invention, a stay suture retainer 45 is affixed to one of the jaws of the clamps 16, 17. The stay suture retainer 45 grasps each one of a pair of stay sutures 46, 47 joining together the blood vessel ends 11, 12 on the suture line 13 but spaced apart thereon by an arc of about 120°, in order to lay the walls of the vessel ends in a position appropriate to suturing on front and rear wall segments thereof.

The stay suture retainer 45 comprises first and second arms 48, 49 joined in a U-shape by a part 44 and extending transversely to the clamp 16 as shown in FIGS. 1 and 2 and parallel to the contact surfaces 32, 33 into the space between the clamps 16 and 17. With this orientation, stay sutures from the line 13 are attached to ends of the arms 48 and 49 to immobilize the blood vessel ends 11 and 12.

Each arm 48, 49 of the stay suture retainer comprises a shaft 50 carrying a radially enlarged head 51 thereon and a slidable collar 52 thereabout. The collar 52 has an annular, axial surface 53 which abuts against a corresponding surface 54 on the underside of the head 51. The collar 52 is biased into abutment with the head 51 by a coil spring 55 about the shaft 50 and bottomed upon a base member 56. The spring 55 need not be unusually strong, since generally little tension is maintained upon the stay sutures 46, 47 by the surfaces 53, 54, as shown in FIG. 3. It is also feasible to use a plurality of independent washers in place of the collar 52, in order that the stay sutures 46 or 47 may be captured between any two of them when placed there by the surgeon's forceps.

In a second configuration of the microvascular surgical clamp apparatus of the invention, shown in FIGS. 4 and 5, clamps 116 and 117 similar to those of clamps 16 and 17 of FIGS. 1 and 2 have the guide bracket 19 on each moved forwardly along the second graspable portion 26 thereof to be fixed adjacent the crossed connecting portions 28, 29. Moving the guide bracket 19 forwardly permits ready adjustment of the spacing of the clamps 116 and 117 along the bar 15 by sideward pressure 142 or 143 applied at the tips of the jaws 30, 31.

Other variations shown in the embodiment of FIGS. 4 and 5 from those of FIGS. 1 and 2 include the use of a plurality of washers 152 in place of collars 52 on the arms 48 and 49 of the stay suture retainer 145, and also making the arms 48 and 49 separately and attaching them separately to the jaw 31 rather than having them joined together in a U-form by part 44 as in FIGS. 1 and 2. Where the arms 48, 49 are separate, they may be joined different ones of the jaws 30, 31 of the clamps 16, 17, or 116, 117. Further, an abutment member 60 is shown added to the guide bracket 19 in the forward position of FIG. 5, for abutting the opposite interior surface 40a of the graspable portions 25, 26 of the clamp 115. The abutment member 60 prevents opening of the clamp 115 at the jaws 30, 31 thereof much beyond the spacing shown in FIG. 5, which is adequate to grasp and clamp a blood vessel therein. Application of too great a squeezing force 61, 62 upon the graspable portions 25, 26 can distort the spring 27 so that the jaws 31, 32 no longer exert a sufficient clamping pressure to the blood vessel end engaged therein. Finally, FIG. 5 shows pads 65 of a sponge or foam rubber material applied to the interior surfaces 31, 32 of the jaws 30, 31 to avoid mechanical damage to the blood vessel walls. In practice, a single piece of sponge or foam rubber is applied between adhesively-coated contact surfaces 32, 33 and the adhesive allowed to set, whereupon the rubber is split longitudinally into two pads 65 as shown.

A third embodiment of the microvascular surgical clamp apparatus is disclosed in FIGS. 6 through 8. In this third embodiment, each clamp 216 and 217 of the assembly 210 comprises an elongate shaft 70 carrying on a forward end thereof a first jaw 230 having a contact surface 232 transverse to the longitudinal direction of the shaft 70. Carried slidably upon the shaft 70 is a second jaw 321 having a collar portion 71 for orientation to the shaft 70. A second contact surface 233, on the jaw 232, engages the first contact surface 232 in parallel, flat relationship. A rearward shoulder 72 of the collar portion 71 is engaged by a coil spring 227 which biases the jaw 231 into engagement with the jaw 230. Tension of the spring 227 is adjustable by an internally threaded nut 73 which engages a correspondingly threaded portion 74 of the shaft 70. A pin 75 on a tip end of the jaw 230 extends parallel to the shaft 70 to pass into an alignment aperture 76 formed in the second jaw 231. The pin 75 both prevents a vessel from sliding out of the clamp 216 to the left as in FIG. 8 but also aligns the jaws 230 and 231 together where the shaft 70 is cylindrical above the threaded portion 74. Were a square shaft 70 to be used with a correspondingly shaped collar portion 71, the pin 75 and corresponding aperture 76 could be dispensed with. However, due to the small size (8–10 mm total length and about 2 mm useable jaw length normal to the shaft 70), manufacturing requirements may dictate that the entire shaft 70 be threaded, that is, that the shaft 70 be a threaded rod. Further, having a rounded shaft 70 permits the jaw 231 to be swiveled out of the way when the blood vessel end 11 or 12 is to be released, as upon completion of suturing.

Where the individual clamps 216 and 217 are to be used together, they are assembled upon a rigid bar 215 as in the embodiments of FIGS. 1 and 2. Either or both of the clamps 216, 217 may be affixed to a guide bracket 219 as by soldering or brazing as at 241. Due to the small size of the clamps 216, 217, however, in some instances it will be preferable to solder one of the clamps directly to the bar 215. In any event, the two shafts 70, 70 of the clamps 216, 217 will be held in a coplanar relationship with one another and with the bar 215, just as were the clamps 16 and 17 of FIG. 1.

Further in accordance with the principles of the invention, a stay suture retainer 245 is affixed to the second jaw 231 along its collar portion 71 to extend generally between the two clamps 216, 217, and parallel to the plane of the shafts 70, 70 and the bar 215. The first and second arms 248, 249 of the stay suture retainer 245 are similar to those of FIGS. 1 through 5, but due to the smaller size thereof and limited attachment area along the collar 71 of the second jaw 231 are preferably made in one piece with a U-form including a bottom portion 244 extending generally parallel to the shaft 70.

In use, any of the three embodiments of clamps disclosed herein are prepared by adjusting tension of the spring 27 or 227 in accordance with the size of the blood vessel ends to be joined so that the maximum permissible pressure (30 gm/cm²) is not exceeded. Once the vessel attachment site is prepared, one vessel end 11, 12 is clamped in each clamp 16, 17 so that the ends may be brought into engagement at a suture line 13. After irrigation of the vessel ends as described in the Ostrup article, the stay sutures 46 and 47 are each passed through the vessel ends 11, 12. An end of each suture is passed to the respective arm 48, 49; 248, 249 of the respective stay suture retainer 45, 145, or 245. Following the close suturing of the 120° segment of the suture line 13 on one side of the vessel, the entire apparatus 10, 110, or 210 is rotated about the axis of the vessels 11, 12 so that the completed portion of the suture line lies underneath and the interior of the vessel ends lies exposed for joining by further suturing about the remaining 240° of the suture line 13. Because the stay sutures are affixed directly to the clamp apparatus 10, 110 or 210 no separate manipulation thereof is required. Upon completion of the suturing, the stay sutures 46, 47 may be removed or cut short about the walls of the vessels 11, 12. As suggested in Ostrup, one or both of the clamps 16, 17; 116, 117; or 216, 217 are released and blood allowed to flow to the suture line 13 and to seal same by controlled bleeding therethrough. In this regard, the individual clamps of each pair are manipulatable independently of the other, so that the downstream side may be unclamped first. With the clamps of FIGS. 6 through 8, where a round shaft 70 is employed, the second jaw 231 may be moved rearwardly on the shaft 70 and then swiveled so that the contact surfaces 232, 233 no longer engage in the area of the blood vessel, to relieve same from any clamping force. Since the clamps of the present invention have no soldered or brazed connections at points of flexibility, and they are otherwise of entirely metal construction except for the replaceable rubber cushion 65, the clamps are reuseable indefinitely and repeatedly following normal sterilization. However, it is also intended that any of the clamps, especially the small clamps of FIGS. 6 through 8, be so inexpensive to produce that they may be discarded after each use.

Although various minor modifications may be suggested by those versed in the art, it should be understood that I wish to embody within the scope of the patent warranted hereon all such modifications as reasonably and properly come within the scope of my contribution to the art.

I claim as my invention:

1. A microvascular clamp apparatus comprising:
    an elongated, rigid bar;
    a pair of clamps spaced apart along said bar and each carrying a pair of substantially parallel-closing, relatively-movable jaws;
    guide and attachment means on each of said clamps for retaining said clamps on said bar in transverse relation thereto in a substantially coplanar relationship to one another and at a selected spacing from one another;
    spring means on each of said clamps for biasing at least one of the relatively-movable jaws of each pair into contact with the other at a contact surface; and
    a stay suture retainer affixed to said pair of clamps to extend substantially in plane of the clamps and bar, said stay suture retainer comprising
      first and second arms carried on at least one of said jaws and lying substantially in said plane and adjacent but on opposite sides of a line extending between said contact surfaces of the jaws of the clamps, and
      attachment means on each of said arms for removably engaging a stay suture,
    whereby two ends of a blood vessel clamped at said contact surfaces by said jaws are immobilized for connection together by stay sutures placed through said ends and engaged by said attachment means on said stay suture retainer arms.

2. A microvascular surgical apparatus as defined in claim 1, wherein the rigid bar has a constant cross-sectional area and at least one of said guide means is slidably engaged about said bar for varying the selected spacing of the clamps.

3. A microvascular surgical apparatus as defined in claim 1, wherein the contact surfaces have a non-slip surface treatment.

4. A microvascular surgical apparatus as defined in claim 3, wherein the surface treatment comprises a sponge rubber coating.

5. A microvascular surgical apparatus as defined in claim 1, wherein each of the clamps comprises:
a pair of elongate graspable portions joined together on rearward ends thereof by said spring means,
    said spring means comprising at least one arcuately curved, resilient member serving as a hinge between the graspable portions and biasing them apart;
a pair of crossed connecting portions each fixed at a rearward end to one of the graspable portions and at a forward end to an opposite one of said jaws, whereby a force applied to the graspable portions against the bias of the spring means to move the graspable portions together will open the jaws; and wherein
said guide means is carried on an interior side of one of said graspable portions spaced adjacent the other of said graspable portions.

6. A microvascular surgical apparatus as defined in claim 5, wherein the spring means is formed integrally with said graspable portions and has a portion of reduced width formed therein for reducing a maximum bias extertable by said spring means to a safe limit.

7. A microvascular surgical apparatus as defined in claim 5, wherein said guide means is carried on one of said graspable portions adjacent the spring means, whereby a sideward force exerted upon said jaws parallel to the rigid bar will tend to cock the guide means and prevent sliding of the clamp along said bar.

8. A microvascular surgical apparatus as defined in claim 5, wherein said guide means is carried on one of said graspable portions adjacent the crossed connecting portion related thereto, whereby a sideward force exerted on said jaws parallel to the rigid bar will slide the clamp along the rigid bar for adjusting the spacing of the clamps.

9. A microvascular surgical apparatus as defined in claim 5, wherein the graspable portion carrying the guide means is attached via its respective crossed connecting portion to one of the jaws carrying one of the stay suture retainer arms.

10. A microvascular surgical apparatus as defined in claim 1, wherein the stay suture retainer comprises a U-shaped member including said first and second arms and having a base attached to one of said jaws on a surface opposite the contact surface thereof.

11. A microvascular surgical apparatus as defined in claim 1, wherein the first and second arms of the stay suture retainer are separately attached to the jaws.

12. A microvascular surgical apparatus as defined in claim 1, wherein the attachment means of the stay suture retainer further comprises:
a radially-enlarged head on said arms;
a slidable collar received coaxially on said arm; and
a coil spring means bottomed on said arm at a point spaced from said head and biasing said collar against said head,
whereby a stay suture may be selectively and positively gripped between said collar and said head during suturing of blood vessel ends.

13. A microvascular surgical apparatus as defined in claim 1, wherein the clamps each comprise:
an elongate shaft affixed to said guide means;
a first jaw affixed to an end of the shaft opposite the guide means;
a second jaw having a collar received slidably on the shaft between the guide means and first jaw;
a nut engaged with said shaft and spaced between the jaw and collar member and the guide means; and wherein
said spring means comprises a coil spring bottomed upon said nut and biasing said second jaw toward said first jaw.

14. A microvascular surgical apparatus as defined in claim 13, wherein the shaft and the nut are cooperatively threaded, whereby the spring biased on the second jaw is adjustable by spacing of said nut along the shaft.

15. A microvascular surgical apparatus as defined in claim 13, wherein the stay suture retainer arms are affixed to the second jaw and the collar thereof.

16. A microvascular surgical apparatus as defined in claim 13, wherein the first jaw has a pin extending transversely therefrom and parallel to said shaft and said second jaw has an aperture formed therein for receiving said pin, whereby the two jaws may be aligned when in use.

17. In a U-shaped microvascular surgical clamp apparatus having a pair of clamp members extending in a plane transversely from a holding bar, each of the clamp members having substantially parallelclosing jaws, the improvement of a stay suture retainer attached thereto, comprising:
a pair of spaced-apart arms each affixed to one of said jaws of said clamp members and extending in said plane and between the clamp members;
an enlarged head on each of said arms;
a shiftable collar carried on each of said arms and selectively abutting against said enlarged head; and
spring means for biasing said collar against said enlarged head,
whereby two stay sutures extending from blood vessel ends being connected together in said clamp apparatus are positively gripped and immobilized with said vessel.

18. A microvascular surgical clamp apparatus comprising:
a shaft;
a first jaw fixed to the shaft on one end thereof, the jaw having a contact surface adjacent and transverse to the shaft;
a slidable second jaw having a contact surface parallel to the first jaw and movable along the shaft and into contact with the first jaw;
a spring means biasing said second jaw into engagement with said first jaw, the spring means being bottomed on said shaft; and
a stay suture retainer affixed to one of said first and second jaws, the stay suture retainer comprising a pair of arms each extending transversely of said shaft and said contact surfaces and spaced apart from one another, and attachment means on an end of each of said arms spaced from a line of said said shaft, said attachment means being adapted to engage a stay suture end to immobilize ends of a blood vessel being joined adjacent said clamp.

19. A microvascular surgical apparatus as defined in claim 18 wherein said spring means is bottomed on a nut threadably engaged with a threaded portion of said shaft, being variably spaced via said threads along said shaft to vary the bias on said second jaw.

20. A microvascular clamp apparatus comprising: an elongated, rigid bar;

a pair of clamps spaced apart along said bar and each carrying a pair of substantially parallel-closing, relatively-movable jaws;

guide and attachment means on at least one of said clamps for retaining said clamps on said bar in transverse relation thereto in a substantially coplanar relationship to one another and at a selected spacing from one another;

spring means on each of said clamps for biasing at least one of the relatively-movable jaws of each pair into contact with the other at a contact surface; and a stay suture retainer affixed to said clamp apparatus to extend substantially in the plane of the clamps and bar, said stay suture retainer comprising first and second arms carried on said clamp apparatus, and lying substantially in said plane and adjacent but on opposite sides of a line extending between said contact surfaces of the jaws of the clamps, and attachment means on each of said arms for removably engaging a stay suture, whereby two ends of a blood vessel clamped at said contact surfaces by said jaws are immobilized for connection together by stay sutures placed through said ends and engaged by said attachment means on said stay suture retainer arms.

* * * * *